United States Patent [19]
Klegerman et al.

[11] Patent Number: 5,712,123
[45] Date of Patent: Jan. 27, 1998

[54] MIXTURE HAVING ANTITUMOR ACTIVITIES

[75] Inventors: Melvin E. Klegerman, Chicago; Michael J. Groves, Deerfield; Ronghua Wang, Hinsdale, all of Ill.

[73] Assignee: Board of Trustees of The University of Illinois, Urbana, Ill.

[21] Appl. No.: 540,002

[22] Filed: Oct. 6, 1995

Related U.S. Application Data

[63] Continuation of Ser. No. 319,515, Oct. 7, 1994, abandoned.

[51] Int. Cl.$^6$ ............................ C12P 19/00; A61K 39/02; A61K 39/04; C12N 1/00
[52] U.S. Cl. ............ 435/72; 424/234.1; 424/248.1; 435/863; 514/23; 514/54; 536/123; 536/123.1
[58] Field of Search ................. 424/248.1, 234.1; 435/72, 863; 536/123, 123.1; 514/54, 23

[56] References Cited

U.S. PATENT DOCUMENTS

| | | |
|---|---|---|
| 4,639,516 | 1/1987 | Misaki et al. ........................ 536/123 |
| 4,726,947 | 2/1988 | Shimada et al. .................... 424/248.1 |
| 5,488,040 | 1/1996 | Jamas et al. ........................ 514/54 |

OTHER PUBLICATIONS

Lou et al. Anticancer Res. (Jul.–Aug. 1994) vol. 14, pp. 1469–1476.
Mizuno et al. Nippon Nogei Kagaku Kaishi (J. Ag. Chem. Soc. of Japan) (1984) vol. 58, pp. 871–880 (Abstract–Caplus).
Mansell et al. J. Natl. Cancer Inst. (1975) vol. 54, pp. 571–580.
Hunter et al. J. Natl. Cancer Inst. (1978) vol. 60, pp. 419–422.

*Primary Examiner*—Leon B. Lankford, Jr.
*Assistant Examiner*—Christopher R. Tate
*Attorney, Agent, or Firm*—McDonnell Boehnen Hulbert & Berghoff

[57] ABSTRACT

A purified hot-water extract from *Mycobacterium bovis* (BCG vaccine) has been found to have significant antitumor activity against a mouse bladder tumor model and a murine sarcoma in vivo, but not in vitro. The material, termed PS1A1, has an approximate molecular weight of between 60 and 90 kDa, is freely soluble in water, but has low solubility in acetone or ethanol, and is remarkably heat-stable.

6 Claims, 11 Drawing Sheets

FIG. 2

| Fractions | Titer, mg/kg | Specific activity, U/mg |
|---|---|---|
| PS1 | 80 | 500 |
| PS1A | <38 | >1000 |
| PS1A1 | <<2 X $10^{-5}$ | >>2 x $10^6$ |

FIG. 10

| proton | Chemical shift (p.p.m.) | | |
|---|---|---|---|
| | 1→6-α-Glcp | 1→6-α-Glcp | 6-Glcp |
| H1 | 4.96 | 5.39 | 4.96 |
| H2 | 3.56 | 3.58 | 3.55 |
| H3 | 3.71 | 3.68 | 3.71 |
| H4 | 3.50 | 3.94 | 3.41 |
| H5 | 3.90 | ND | 3.83[a] |
| H6 | 3.98 | ND | 3.83[a] |
| H6' | 3.74 | ND | 3.76[a] |

ND: not determined

[a] - chemical shifts assigned on the basis of their comparison with α-glucose 5,712,123

1

MIXTURE HAVING ANTITUMOR ACTIVITIES

REFERENCE TO RELATED APPLICATIONS

This is a continuation-in-part of U.S. Ser. No. 08/319,515 filed on Oct. 7, 1994, abandoned, which is incorporated herein by reference. Applicants claim priority to the filing date of the aforementioned application.

SUMMARY OF THE INVENTION

Tice® substrain BCG is used clinically as an immunotherapeutic agent against superficial bladder cancer. A boiling water extract of this BCG showed antitumor activity against a murine S180 sarcoma model and was fractionated into three fractions, A, B and C, by the use of Sephadex LH-20 chromatography. An antitumor glucan, PS1A1, was isolated from fraction PS1A with Sephadex G-75. The molecular weight of PS1A1 was between 65 and 87 kDa by Sephadex G-100 chromatography and 64.5 kDa by electron spray mass spectroscopy. The structure of PS1A1 was investigated by one- and two-dimensional n.m.r. spectroscopy and methylation analysis and was demonstrated to be primarily 1→6-α-linked glucose units. PS1A1 exhibits potent antitumor activity.

BACKGROUND OF THE INVENTION

An attenuated strain of *Mycobacterium bovis*, Bacillus Calmette-Guerin (BCG vaccine), has been used as a tuberculosis vaccine for more than 70 years. The inverse relationship between cancer and tuberculosis was established as early as 1929 by Pearle and the first trial of BCG vaccine against cancer was carried out by Holmgren in Sweden in 1935. The antitumor activity of BCG has been demonstrated consistently in recent years and commercial sources of BCG have been approved by the United Stated Food and Drug Administration as an immunotherapeutic agent for the treament of superficial bladder cancer. The vaccine has also shown efficacy against other tumors, such as melanoma, lung cancer and leukemia.

BCG's anticancer activity has been attributed to a nonspecific stimulation of the lymphoreticuloendothelial system. The nature of the molecular components responsible for the antineoplastic properties of BCG vaccine remains uncertain.

Adverse effects of BCG immunotherapy, such as urethritis, disseminated mycobacterioses and enhancement of tumor growth, can be attributed to the use of whole, living, organisms and it would be advantageous to isolate and identify any antineoplastic components for clinical application.

SSM, a mycobacterial arabinomannan immunomodulator with antineoplastic activity, was isolated by Suzuki et al from the Aoyama B strain of *M. tuberculosis*. This material is similar, if not identical, to Zeria Pharmaceutical's Z-100 which was reported to have been tested clinically. An apparently analogous material, lipoarabinomannan (LAM) has been isolated from *M. leprae* and *M. tuberculosis* and has been reported to induce macrophage secretion of tumor necrosis factor.

Recent studies indicated that BCG contains variable proportions of immunomodulators that may have contradictory influences on the growth of malignant tumors and that the antineoplastic activity can be adoptively transferred with splenocytes in the S180 murine sarcoma model. A glycolipid fraction (termed PS1~) was extracted from a commercial substrain of BCG, by a method similar to that utilized by Suzuki et al for the extraction of SSM from *M. tuberculosis*, which exhibits antitumor activity in a mouse sarcoma model, but not on the malignant cells in vitro. Therefore, like SSM, PS1 appears to posses antitumor activity, but differs from SSM in many respects, including the fact that it is obtained from BCG, a nonvirulent organism for which safe, large-scale production methods are established.

PS1, obtained from the Tice® substrain of BCG, appears to consist of a complex mixture of polysaccharides and glycolipids and exhibits anticancer activity in the mouse S180 sarcoma assay. PS1 is extremely water-soluble, being nearly insoluble in ethanol or acetone, and is not directly cytotoxic for tumor cells. SDS-PAGE indicated that PS1 contains only trace quantities of LAM and arabinose accounted for only about 4% of total carbohydrate. Carbohydrate and fatty acid analyses also indicated that PS1 could contain appreciable amounts of glucan, lipomannan (LM), phosphoinositolmannoside (PIM) and mycoside B, as well as some arabinomannan and arabinogalactan. Polymyxin B-sepharose adsorption, petroleum ether extraction and saponification of PS1 did not decrease the antitumor activity, indicating that biological activity may be attributable to a polysaccharide.

PS1 components contain at least 50% carbohydrate, consisting mainly of glucose, arabinos, galactose and mannose, and about 10% lipid that may correspond to phosphatidylinositol. It shares chemical and biological properties with an arabinomannan isolated from *M. Tuberculosis*, but it contains only trace quantities of lipoarabinomannan (LAM). PS1 appears to be non-toxic in mice up to a dose of 5 mg/kg, while as little as 70 µg/kg is sufficient to inhibit tumor formation significantly.

A mixture termed PS1A1 has been isolated from PS1. PS1A1 demonstrates potent antitumor activity and is the subject of the present invention.

PREPARATION AND CHARACTERIZATION OF PS1

Extraction Procedure. Lyophilized Tice®—substrain BCG vaccine (lot105B153c, manufactured at The Institute for Tuberculosis Research in 1983, stored at –20° C.) ATCC Catalog No. 35743, deposited with American Type Culture Collection, Rockville, Md. was reconstituted in sterile water and washed twice (by centrifugation at 30,000×g for 20 minutes) with Dulbecco's phosphate buffered saline (PBS), resuspended with 20 mL deionized, distilled water (DD $H_2O$) per mg wet weight cells and heated in a boiling water bath for two hours. After cooling, the solution was passed through a 0.45 µm membrane filter (Nalge Co., Rochester, N.Y.) and concentrated 400–800× using a rotary evaporator (Valley Electromagnetics Corp., Spring Valley, Ill.) under reduced pressure to produce a crude extract.

Fractionation of the crude extract. The crude extract was fractionated by dissolving 3 mg of the extract in 1 mL distilled water and chromatographing on a 2.5×50 cm (245 mL) Sephacryl S-200 HR column (Pharmacia LKB Biotechnology, Piscataway, N.J.) at a flow rate of 10 mL/hr. Two-mL fractions were collected with BioRad model 2110 fraction collector (Bio Rad Laboratories, Richmond, Calif.). A molecular weight calibration curve was determined by monitoring ($A_{280}$) elution of ferritin, albumin, carbonic anhydrase and cytochrome c under identical conditions. For in vivo bioassay, fractions were prepared by dialysis of the crude extract through Spectra/Poe 2 tubing (12–14 kDa MW cutoff; Spectrum Med. Ind., Los Angeles, Calif.) against IL DDH$_2$O for 24 hours. The retentate and dialyzate (after concentration to about 10 mL by rotary evaporation) were lyophilized, weighed, reconstituted with PBS and sterilized by filtration (0.2 µm Acrodise syringe filters, Gelman Sciences, Ann Arbor, Mich.) prior to bioassay.

Separation of the high molecular weight fraction (PS1). The crude extract was dialyzed against 1 L of water through Spectra/Por 2 tubing with two changes over 24 hours, followed by lyophilization using a Labconco Lyph-Lock 4.5 Freeze Drying System (Labconco Corp., Kansas City, Mo.). This lyophilized material was termed PS1 and was used throughout subsequent experimentation. The yield from 12 separate lots of PS1 was 12.0%=0.7% (SD) of the dry bacterial weight. PS1 was also obtained in 11% yield by refluxing 2 ampoules of Tice BCG, lot 105×1, in 80 ml, DDH$_2$O for two hours. This material was similar to previously extracted PS1 in terms of HPLC profile and carbohydrate content.

Carbohydrate analyses. Hydrolysis, derivitization and gas chromatography (GC) of polysaccharides in PS1 was performed by previously described methods. Total sugar content of samples was measured by the phenol-sulfuric acid assay (PSA) using D-arabinose (Fluka Chem., Ronkonkoma, N.Y.) as standard.

Solubility of PS1. The lyophilized product was freely soluble in distilled water at room temperature: therefore aqueous solubility was not measured. Dry PS1 (10 mg) was added to 1.0 mL of acetone or 1.0 mL of ethanol in 1.5-mL polypropylene microcentrifuge tubes (Fisher Scientific, Itasca, Ill.). The sealed tubes were agitated for 5 minutes at room temperature with a vortex mixer and centrifuged at 13,000 rpm in a MicroCentaur centrifuge (Accurate Chemical and Scientific Supply, Westbury, N.Y.) for 10 minutes. The concentration of PS1 in the supernates was determined by PSA.

Determination of lipids and protein in PS1. PS1 (2.0 mg/mL) was dissolved in distilled water, 80 µl, of this solution was saponified with sodium hydroxide solution, methylated with methanolic hydrochloric acid and extracted with methyl-tertiary-butyl ether/hexane as described by Olson et al. The fatty acid methyl esters were separated and quantitated by GC using a Hewlett Packard (Avondale, Pa.) Model 5890A gas chromatograph interfaced with a Model 7673A automatic sampler, Model 3392A integrator, Model 7673A Controller and personal computer. Protein content of PS1 was measured with the BCA protein assay reagent according to the instruction of the manufacturer (Pierce, Rockford, Ill.).

High Performance Liquid Chromatography (HPLC). Reverse-phase HPLC was performed with a Waters system (Millipor Corp., Milford, Mass.), consisting of a model 600 Multisolvent Delivery System, a model 490 Programmable Multiwavelength Detector and a model 745 Data Module. PS1 (2.6 µg in 10 µL of DDH$_2$O) was applied to a Progel-TSK Amido 80 column (250×4.6 mm i.d.; Supelco, Inc. Bellefonte, Pa.) and eluted with 75% acetonitrile/25% water at a flow rate of about 1 mL/min. while monitoring A$_{200}$.

Heat Treatment of PS1. PS1 solution (1 mg/mL DDH$_2$O) was sealed in glass ampoules (Wheaton, Millville, N.J.) and autoclaved at 121° C., 15 PSI, or 131° C., 27 PSI, for up to 9 hours in a Barnstead model C2250 laboratory sterilizer (Sybron Corp., Boston, Mass.).

In vivo bioassay. The quantitative murine S180 sarcoma assay was performed as follows. Eight-week-old female CFW Swiss Webster mice were inoculated subcutaneously (sc) in the right flank with 4.8–4800 µg/kg doses of PS1 in volume of 0.1 mL of PBS mixed with an equal volume of PBS containing 2×10$^5$ viable S180 sarcoma cells. Fourteen days after injection, mice were euthanized and dissected in order to assess the incidence of tumors. Intraassay differences in the tumor incidence at 14 days (TI$_{14}$) between the control and test groups were tested for significance by Fisher's Exact Test (FET) and by the chi-squared test for the total of several assays. The bioassay was also performed by administering various doses of PS1 through several alternative routes two hours after sc S180 cell challenge. Besides intraperitoneal (ip) injection, ipsilateral and contralateral sc injections were at the site of tumor challenge and in the left flank, respectively; intramuscular (im) and intravenous (iv) injections were in the right thigh and the tail vein, respectively, and oral administration (po) was by gavage using Perfektum® 18 G×3 in. animal feeding needles (Popper and Sons, Inc., New Hyde Park, N.Y.).

Immunoelectrophoresis. Standard (IEP) and crossed (CIE) immunoelectrophoresis of PS1 and Tice BCG culture filtrates vs. Dako anti-BCG serum (Dako Corp., Carpenteria, Calif.) were performed by previously published methods. IEP was carried out at 50 v for one hour.

Sephacryl S-200 HR chromatography of the crude aqueous extract of BCG yielded three discrete polysaccharide fractions of 22.4, 5.4 and 2.4 kDa average molecular weight. Testing of the Spectra/Por 2 retentate and dialyzate in the S180 sarcoma bioassay revealed that most of the biological activity of the crude extract was associated with material MW>12 kDa, designated PS1.

The lyophilized PS1 was a white to off-white fluffy power and contained less than 3% protein. Four assays indicated that PS1 consists of approximately 50% carbohydrate. However, hexoses such as D-glucose and D-mannose exhibited only one-sixth to one-fifth the extinction as D-arabinose in this assay, indicating that the carbohydrate content of PS1 could be appreciably higher. GC carbohydrate analysis indicated that glucose comprised most of the hydrolyzable sugar in PS1, with appreciable amounts of mannose, galactose and arabinose also present in decreasing order of abundance. Saponification and GC analysis of fatty acids yielded results consistent with an approximate content of 10% phospholipid containing palmitic and stearic acids as the predominant esterified fatty acids. PS1 exhibited a single UV peak above 220 nm at 255 nm, with a 0.1% extinction coefficient of 1.6, indicating a nucleic acid content of 5%. Although PS1 was freely soluble in water, the solubility in 95% ethanol or acetone was less than 0.5 mg/mL.

Tumors in mice receiving either the 4.8 mg/kg or 480 µg/kg does were consistently significantly inhibited ($X^2$=32.6 and 20.9, respectively; P<0.001), while tumor incidence in mice receiving the 48 µg/kg or 4.8 µg/kg doses were not significantly different from the controls ($X^2$=1.434 and 0.765, respectively; P>0.05). The titer, defined as the lowest quantity of assayed material causing a significant inhibition of tumor incidence, is 74.4 µg/kg or about 1.86 µg per mouse. If a unit of activity is defined as the last value, the specific activity would be 538 U/mg dry weight, corresponding to a yield of 65 U/mg BCG dry cell mass. The bioactivity of PS1 prepared from Tice BCG, lot 105×1, by refluxing was similar (titer=135 µg/kg, specific activity=316 U/mg).

Injection of PS1 into mice by alternative routes two hours after S180 tumor challenge showed that contralateral subcutaneous, intravenous and intramuscular dosing are at least as effective as subcutaneous injection at the site of tumor cell inoculation. Furthermore, oral administration of 10 µg of PS1 inhibited formation of S180 tumors more than 50%, although statistical significance was not attained in this experiment. Overall, PS1 efficacy by route appears to be as follows; im>se, iv, po>ip.

Repeated (n=14) reverse-phase HPLC of PS1 on a weak anion-exchange column produced 20 reproducible peaks with retention times ranging from 1.4 to 13.3 min. Autoclaving under conditions as harsh as 131° C. for 9 hours did not significantly affect the antineoplastic activity of PS1. The specific activity of PS1 after maximal autoclaving was 331 U/mg, compared to 417 U/mg for an unheated control preparation.

PREFERRED EMBODIMENT

Extraction and preparation of PS1 from the Tice® substrain of BCG

The contents of twelve ampules of Tice BCG vaccine (lot 105×1, produced by Organon Teknika, Inc., Chicago, Ill.) were dispersed in 480 mL PBS and centrifuged twice at 10,000 k rpm for 10 minutes. The washed BCG cells were extracted in a boiling flask by refluxing with distilled water (500 mL) for two hours. The extract was passed throguh a 0.22 μm membrane filter (Millipore Corporation, Bedford, Mass.) and concentrated by vacuum rotary evaporation. The concentrated water extract was dialyzed through Spectra/Por 2 tubing against 2 L distilled water overnight. The lyophilized material retained in the tubing was termed PS1.

Tlc of PS1

PS1 was spotted on a TLC plate and the plate developed in a solvent system (n-butanol/acetic acid/water, 7:2:3). Two spray reagents were used for the detection of components on the TLC plate: 1) 0.2% ninhydrin in ethanol; 2) a mixture of equal volumes of 20% $H_2SO_4$ and 0.2% 1,3-dihydroxynaphthalene in ethanol.

Sephadex nLH-20 chromatography of PS1

PS1, 15 mg in 1 mL distilled water, was applied to a column (1.5×45 cm) of Sephadex LH-20 gel (Pharmacia Fine Chem., Piscataway, N.J.) equilibrated with distilled water. The column was then eluted with distilled water. Eluent fractions (2 mL) were assayed for carbohydrate by both the phenol/sulfuric acid method and by thin layer chromatography. Three major peaks on the elution profile were idnetified (FIG. 1) and these were termed PS1A through C.

Sephadex G-75 chormatography of PS1A

PS1A from the Sephadex LH-20 column (above) in 1 mL distilled water was applied to a column (1.5×45 cm) of Sephadex G-75 (Pharmacia Fine Chem.) which was equilibrated and eluted with distilled water. Distilled water eluent fractions were assayed by the phenol/sulfuric acid method, above. Four peaks from the elution profile of this fraction could be identified.

Ethanol precipitation of PS1A1

PS1A1, 5 mg, from Sephadex G-75 chromatography was dissolved in 1 mL distilled water, and 10 mL ehtanol (HPLC grade, Fisher Scientific) added. The resulatnt suspension wa centrifuged for 20 minutes at 10,000 rpm. The pellet was dissolved in distilled water, transferred to a vial and lyophilized. This lyophilized material is referenced as PS1A1.

Composition analysis of PS1A1

Alditol acetates of PS1A1 were prepared by the method of Blakeney et al. PS1A1 (2 mg) was dissolved in 1 mL 2M TFA (trifluoroacetic acid). The solution was sealed in an ampoule and autoclaved for 1 hour at 121° C. The autoclaved sample was transferred to a test tube and dried in a flowing air stream overnight. To the dried sample were added 0.1 mL M $NH_4OH$ and 1 mL $NaBH_4$/DMSO (0.1 g/5 mL) and the solution incubated at 40° C. for 90 minutes. Glacial acetic acid (Fisher Scientific), 0.1 mL, 0.2 mL 1-methylimidazole (Aldrich Chemical Co.) and 2 mL acetic anhydride (Fisher Scientific) were added to the test tube, left at room temperature for 10 minutes, and 5 mL of distilled water added. After the solution in the test tube had cooled to ambient temperature, it was partitioned with 1 mL dichloromethane. The dichloromethane phase was then subsequently concentrated in a flowing air stream and used for g.c. analysis.

The alditol acetates were analyzed on a Shimadzu GC-17A gas chromatography instrument using helium as carrier gas, a J & W Scientific DB-23 bonded phase capillary column (30 m×0.25 mm) and a flame ionization detector. The temperature program used was initally set at 150° C., held for one minute after injection and then increased 10° C./min to 240° C. The temperature was held constant at 240° C. for a further 10 minutes until all components had been eluted from the column. Injector and detector port temperatures were both set at 300° C.

Linkage analysis of PS1A1

Methylation of the intact polysaccharide was accomplished with dimethyl lithium according to the procedure of Kvernheim. After methylation, the methylated polysaccharide was purified and isolated using Waters Spe-Pak C18 cartridges as described by Waeghe et al. The purified isolate from this procecdure was reacted with 300 μL 'Superseuteride' (1.0M solution of lithium triethylborodeuteride, in tetrahydrofuran, Aldrich Chemical Co., Inc., Milwaukee, Wis.) for 90 muinutes to selectively deuterate any carboxyl groups in the polysaccharide. The superdeuteride was destroyed at the end of this time with TFA (50 μL, neat) and evaporated to dryness. This was followed by hydrolysis, reduction and acetylation according to the procedure of Harris et al.

G.c.-m.s. analysis of partially methylated alditol acetates was carried out on a Finnegan 4510 g.c.-m.s. The g.c. temperature program was initiated at 90° C. and held for 1 minutes after which the temperature was increased at 10° C./min up to a final temperature of 240° C. This was held constant for a further 10 minutes until all the components had been eluted from the column.

N.m.r. spectroscopy of PS1A1

The sample was initially deuterium-excchanged by lyophilization from $D_2O$, followed by dissolution in 99.98% $D_2O$ (0.5 mL, Ldrich Chemical Co., Inc.). Spectra were recorded on a Bruker AM 400 instrument operating at 400.135 MHz for proton and 100.62 MHz for carbon. Sample concentration was approximately 5 mg/mL with typical sweep widths for normal 1D experiments of 4800 Hz (12 ppm) for $^1H$ amd 23,000 Hz (225 ppm) for $^{13}C$. Chemical shifts were referenced to internal TSP [3-(trimethylsilyl) propionic-2,2,3,3-$d_4$ acid, sodium salt]. Multiple experiments that were carried out included $^{13}C$ DEPT (135°), DQF-COSY, RCT-COSY and HOHAHA experiments. The published spectra were generated using the tools available in NMR Pipe (distributed by Molecular Simulations, Inc.).

Electrospray mass spectrascopy of PS1A1

The molecular weight of PS1A1 was measured on a Hewlett-Packard 5989B electrrospray mass spectrometer equipped with an atmoshphere-pressure ionization source. Sample (0.2 mg/0.2 mL) was dissolved in distilled water to which was added a small amount of sodium chloride and infused into the instrumewnt at 20 μL/min using a micro-HPLC syringe pump.

S180 Mouse Sarcoma Assay

The effect of progressive purification of PS1 on the intineoplastic activity measured using the murine S180 sarcoma assay is summarized in FIG. 2. The antitumor fraction PS1A from Sephadex LH-20 chromatography was further separated on a Sephadex G-75 column. The elution of Sephadex G-75 chromatography, determined by the phenol/sulfuric acid method showed four peaks: PS1A1–4 (FIG. 3). PS1A1 exhibited the greatest antitumor activity, and identification of this antitumor component was therefore attempted.

Structural studies of PS1A1

The g.c. chromatogram of alditol acetates from PS1A1 showed only glucitol, indicating that PS1A1 is substantially a glucan. The molecular weight of PS1A1 was estimated relative to dextran standards (average m.w. 9.3, 39.2 and 73 kDa, Sigma Chemicals, St. Louis, Mo.; 25 and 150 kDa, Fluka Biochemica, Basle, Switzerland) on a Spehadex G-100 column. The results indicated that the molecular weight of PS1A1 was generally between 65 and 87 kDa. Electrospray mass spectroscopy gave the range of molecular weights of PS1A1 between 64.5 kDa and 67 kDa (Wang et al, in preparation).

The total ion chromatogram of partially methylated alditol acetates of PS1A1 generated from g.c.-m.c. analysis is shown in FIG. 4. The EI mass spectra of the peaks in the ion chromatogram indicated that peaks with retention times less than that of peak 950 were impurities. The EI mass spectra of the peaks labelled 950, 1097 and 1261 (FIG. 5) showed that they represented terminal, 6-substitued and 4,6-substitued monosaccharide derivatives, repsectively by comparison to standard mass spectra. Authentic glucose standards were also analyzed and corresponded with the retention times given above. The proton n.m.r. spectrum of PS1A1 (FIG. 6) showed only signals assigned to carbohydrate. The resonances at 4.97 and 5.39 p.p.m. were assigned to anomeric protons while the other protons are seen overlapped between 3.2 and 4.0 p.p.m.

The chemical shifts of protons in the individual glucose residues in PS1A1 were assigned by the analysis of several 2OD n.m.r. experiments including DQF-COSY (FIG. 7), RCT-COSY (FIG. 8) and HOHAHA spectrascopy (FIG. 9). This is illustrated from examination of the DQF-COSY spectrum where it is seen that the anomeric resonance at 4.96 p.p.m. shows an off diagonal element to a signal at 3.56 p.p.m., assigned as H2. H2 then shows a correlation at 3.71 ppm to H3 and this procedure is repeated from H3 through to H6 and H6'. These assigments were then confirmed or new assigments made through the use of RCT-COSY and HOHAHA where additional off diagonal elements to the anmeric resonance can be seen such that in the HOHAHA spectrum (FIG. 9), the signals of H2 to H5 show correlations to the anmeric resonance at 4.96 p.p.m. As can be seen in the RCT spectrum, there are some additional intense cross peaks other than those that form the main component which may be asccribed to some slight impurity. These signals are also evident in the ID proton spectrum but their size is far smaller than would be suggested by the intensity of the cross peaks in the RCT spectrum. The nature of this component would appear to be carbohydrate in origin, possibly monosaccharide glucose from slight decomposition, as the chemical shifts of the various correlations correspond approximately to those of α and β glucose, cf: α-H1=5.21 p.p.m. and β-H1=4.6 p.p.m. The chemical shift assigments for the individual glucose residues are shown in FIG. 10.

The DEPT-135° spectrum of PS1A1 (FIG. 11) shows strong signals typical of an α-1→6-linked glucan with the anomeric carbon resonance at 100.5 p.p.m. and that of C6 at 68.7 p.p.m. In addition to the signals of the α-1→6-linked glucan there are three other weaker signals at 63.5 ($CH_2$), 74.5 and 75.9 p.p.m. (CH) which can be assigned to the terminal glucose residue.

The results of both g.c. analysis and n.m.r spectroscopy indicate that the principle monosaccharide residues of PS1A1 are glucose. On examination of the chemical shift of the anomeric protons it seems that the residues are α-linked since α-linkages commonly show chemical shifts above 4.9 p.p.m. this is confirmed by the value of the H1–H2 coupling constant (approximately 3–4 Hz) which is indicative of an α-linkage by consideration of the Karplus relationship (i.e., Eq-Ax=3–4 Hz, Ax-Ax=8–9 Hz) in monosaccharides. Other coupling constants also confirm that PS1A1 is a glucose homopolymer since H3–H4 shows a large coupling constant (~10 Hz), indicative of the trans-diaxial arrangement in glucose.

From the aforementioned g.c.-m.s. results, it would appear that the polysaccharide PS1A1 is a glucan with predominantly 1→6 linkages. Moreover, some terminal glucose and a branched residue, namely 4,6-substituted glucose, were also observed suggesting that there are occasional branch points along this main chain at postion 4. This is consistent with the n.m.r. results in that a large signal (4.96 p.p.m.) was observed in the $^1$H n.m.r. spectrum which is assigned to the anomeric proton of α-linked 1→6glucose, cf dextran (m.w. 39.2 or 73 kDa, Sigma Chemicals, St. Louis, Mo.) α-1→6 linked glucose at 4.96 p.p.m.

An additional smaller signal at 5.38 p.p.m. is assigned to the anomeric resonance of a glucose residue which is linked to position 4 by consideration of the chemical shift of the corresponding proton in similar molecules such as glycogen and maltose. Integration of the g.c. and n.m.r. peaks corresponding to these branch points indicates that the backbone consists of 1→6 linkages, with 1→4 side chain linkages.

Thus, the PS1A1 mixture contains a polymer that is composed of a plurality of α-D-glucopyranosyl-(1–6)-α-D-glucopyranose units having one or more α-D-glucopyranosyl-(1–4)-α-D-glucopyranose units. PS1A1 is believed to have the following structure:

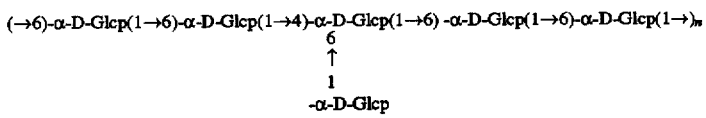

First Medical Use

The invention extends to material from Mycobacterium for use as a pharmaceutical substances as an active ingredient in an antitumor agent. The invention also extends to a pharmaceutical composition containing material from Mycobacterium and optionally, a pharmaceutically acceptable carrier and/or diluent.

Second Medical Use

In a further aspect the invention provides the use of material from Mycobacterium for the preparation of a pharmaceutical composition for treatment against tumor induced diseases.

BRIEF DESCRIPTION OF THE DRAWINGS

FIG. 2. The result of the murine S180 sarcoma assay. Eight-week-old female Swiss-Webster CFW mice were inoculated subcutaneously in the right flank with $3\times10^5$ viable S180 cells mixed with the material to be tested. Fourteen days later, mice were sacrificed, dissected and scored for tumor incidence relative to a control group receiving tumor cells plus PBS. Titer is the lowest quantity of sample producing significant inhibition of tumor formation. One unit of inhibitory activity is defined as the minimum quantity of active principle to cause a significant decrease in the tumor incidence relative to controls, determined by assay of at least three dilutions of each fraction and extrapolation to the point of significance.

FIG. 10. Proton Chemical Shifts of PS1A1. The proton n.m.r. spectrum of PS1A1 (5 mg/0.5 mL $D_2O$) was measured on a Bruker AM 400 spectrometer. Chemical shifts (p.p.m.) were referenced to internal 3-(trimethylsilyl) propionic-2,2, 3,30$d_4$ acid, sodium salt, at room temperature.

Figure 1:
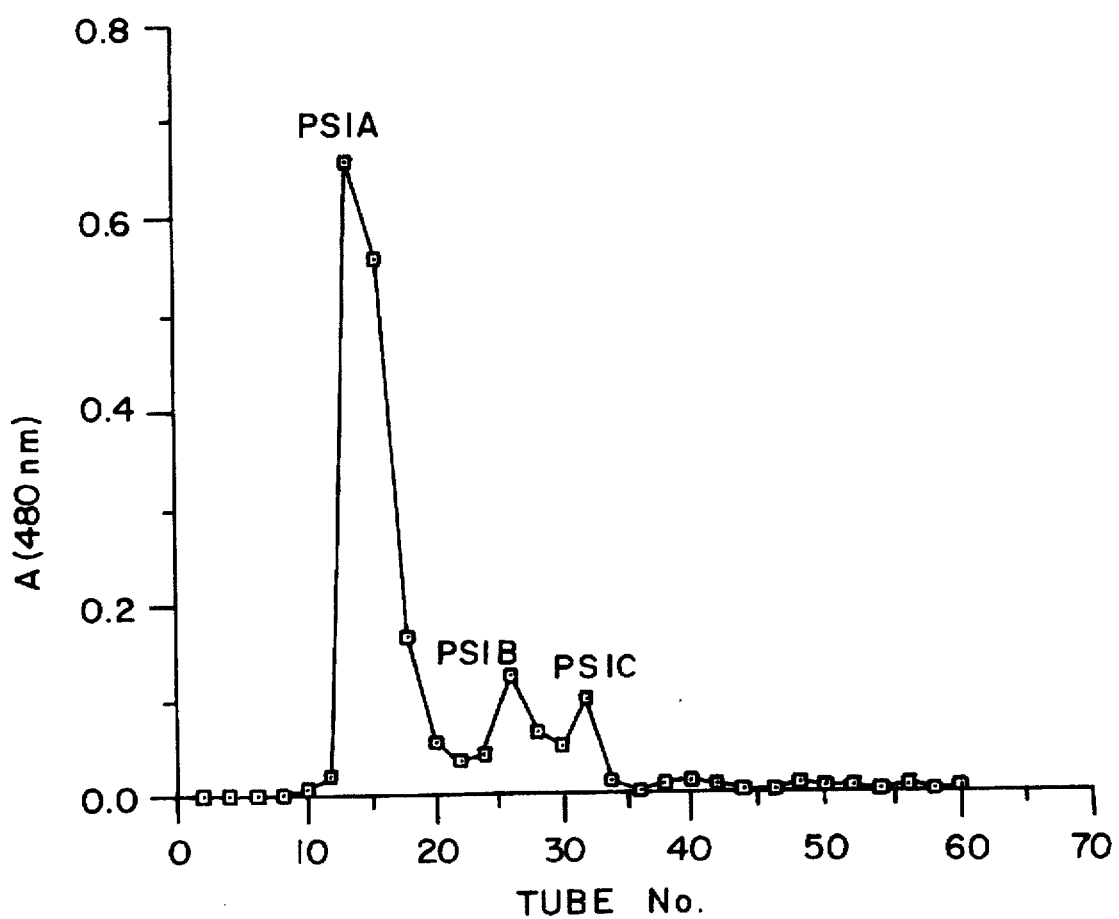
FIG. 1. Elution profile of PS1 on a Sephadex LH-20 column. PS1 was applied to a Sephadex LH-20 column (1.5×45 cm) which was equilibrated and eluted with distilled water at a flow rate of 1 mL/min., and 2 mL fraction were collected. The eluate was assayed for carbohydrates by phenol/sulfuric acid method.
Figure 3:
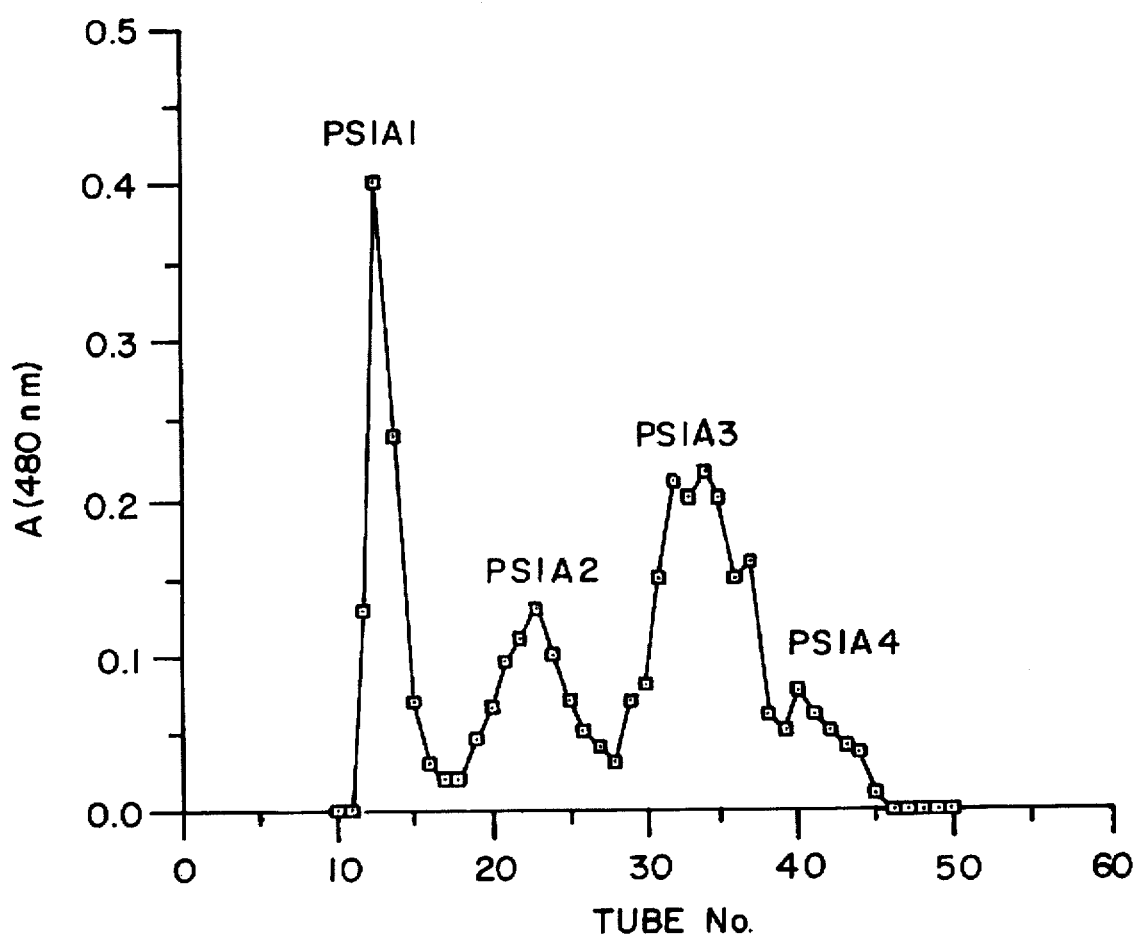
FIG. 3. Elution profile of PS1A on a Sephadex G-75 column. Ps1A was applied to a Sephadex G-75 column (1.5×45 cm) which was equilibrated and eluted with distilled water at a flow rate of 0.5 mL/min., and 2 mL fractions were collected. The eluate was assayed for carbohydrates by phenol/sulfuric acid method.
Figure 4:
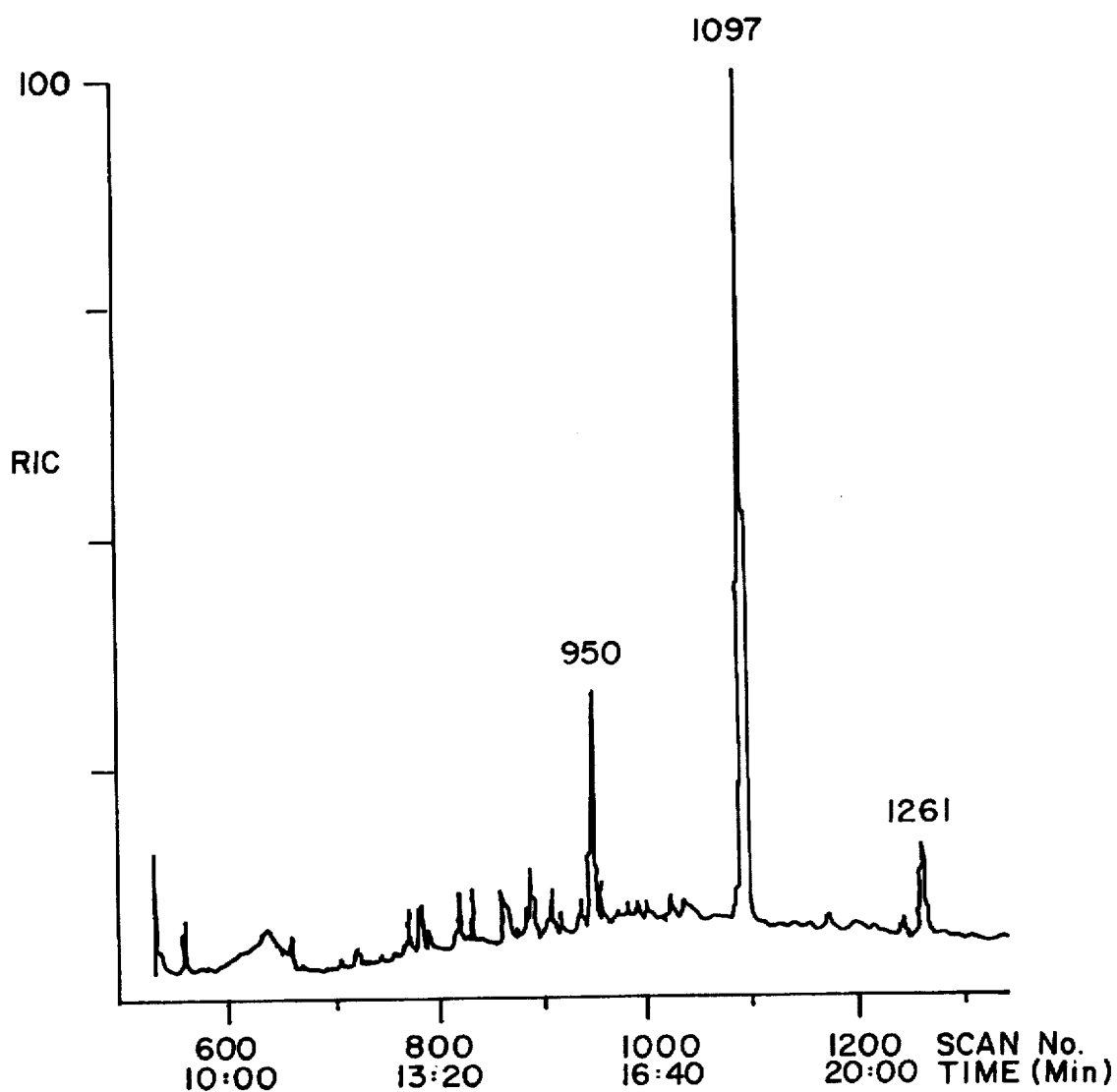
FIG. 4. The total ion chromatogram of partially methylated alditol acetates of PS1A1. Partially methylated alditol acetates of PS1A1 were analyzed with a Finnegan 4510 g.c.-m.s. The peaks labelled with 950, 1097 and 1261 represent terminal, 6-substituted and 4,6 substituted glucose derivatives (see FIG. 4 for their mass spectra). Peaks with retention times less than peak labelled with 950 are impurities.
Figure 5A:
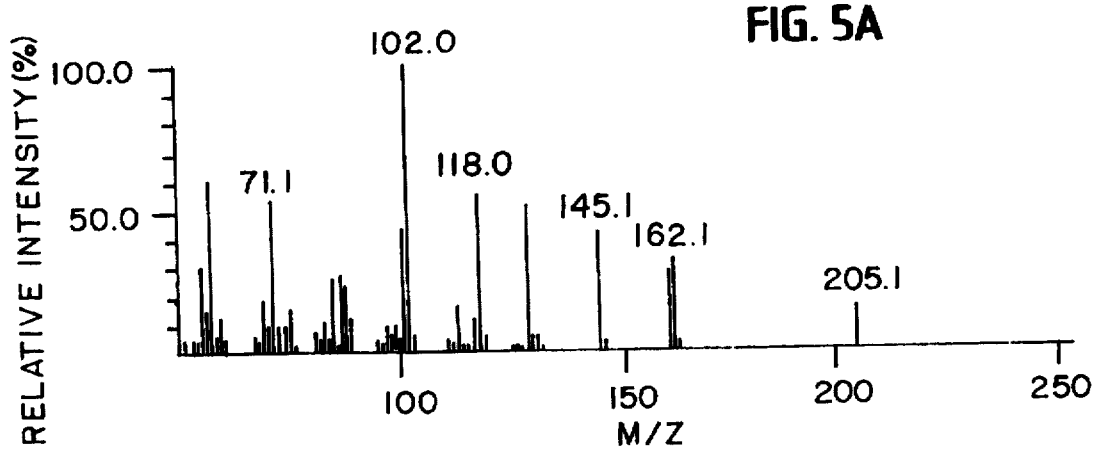
FIG. 5. E.i. mass spectra of partially methylated alditol acetates of PS1A1.
a. 1,5-di-O-acetyl-(1-deuterio)-2,3,4,6-tetra-O-methyl hexitol.
b. 1,5,6-tri-O-acetyl-(1-deuterio)-2,3,4-tri-O-methyl hexitol.
c. 1,4,5,6-tetra-O-acetyl-(1-deuterio)-2,3-dimethyl hexitol.
Figure 5B:
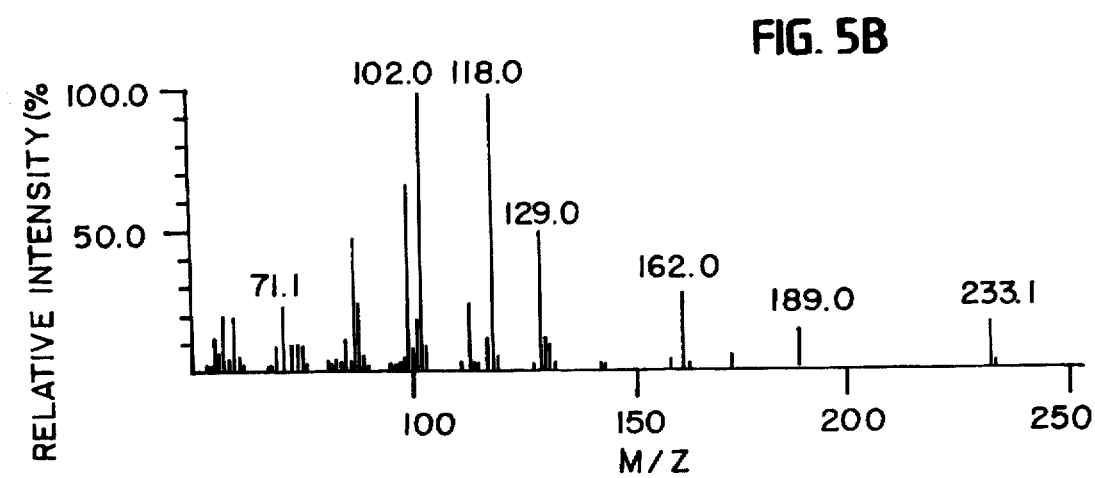
Figure 5C:
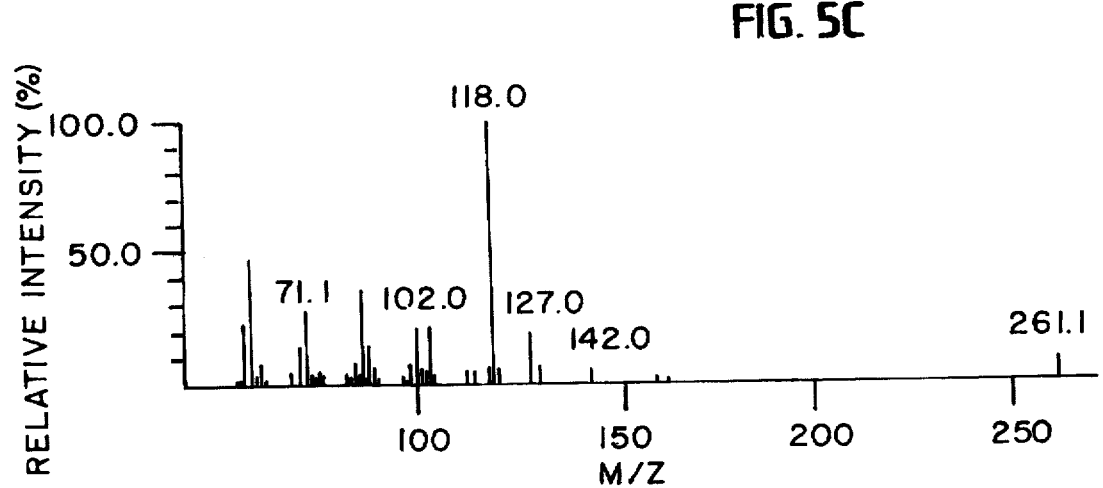
Figure 6:
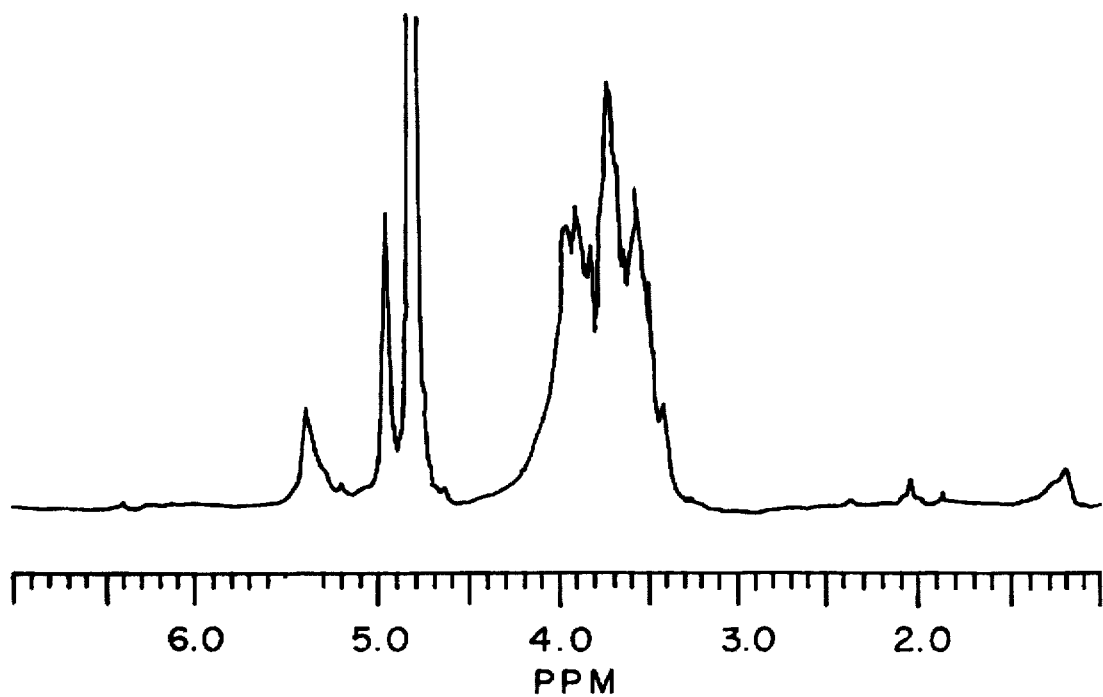
FIG. 6. The proton NMR spectrum of PS1A1. The proton NMR spectrum of PS1A1 in $D_2O$ was measured on a Bruker AM 400 spectrometer. Chemical shifts were referenced to internal standard TSP (3-(trimethylsilyl)-propionic-2,2,3,3-$d_4$ acid, sodium salt).
Figure 7:
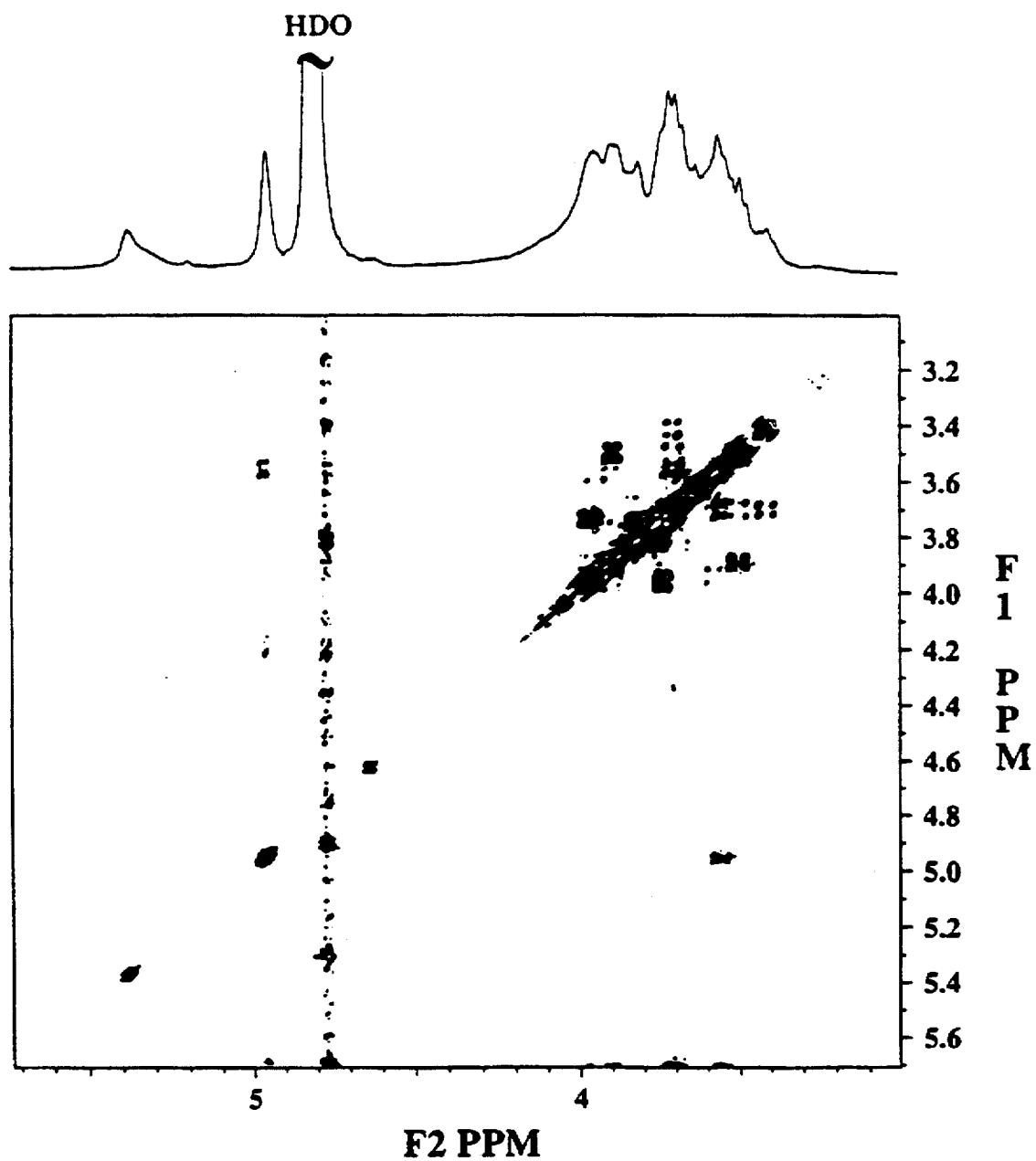
FIG. 7. The DQF-COSY spectrum of PS1A1.
Figure 8:
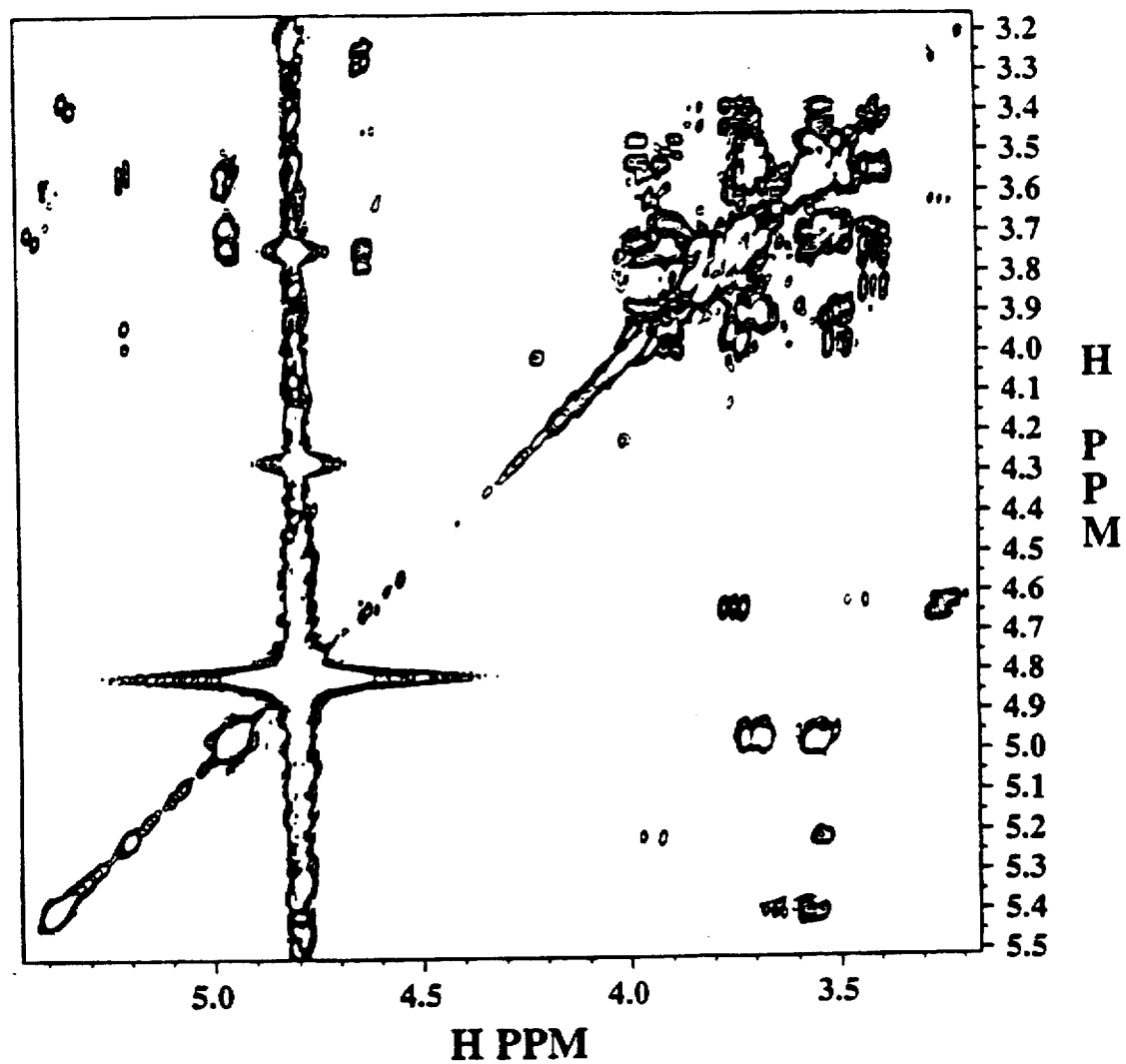
FIG. 8. The Homonuclear RCT-COSY spectrum of PS1A1.
Figure 9:
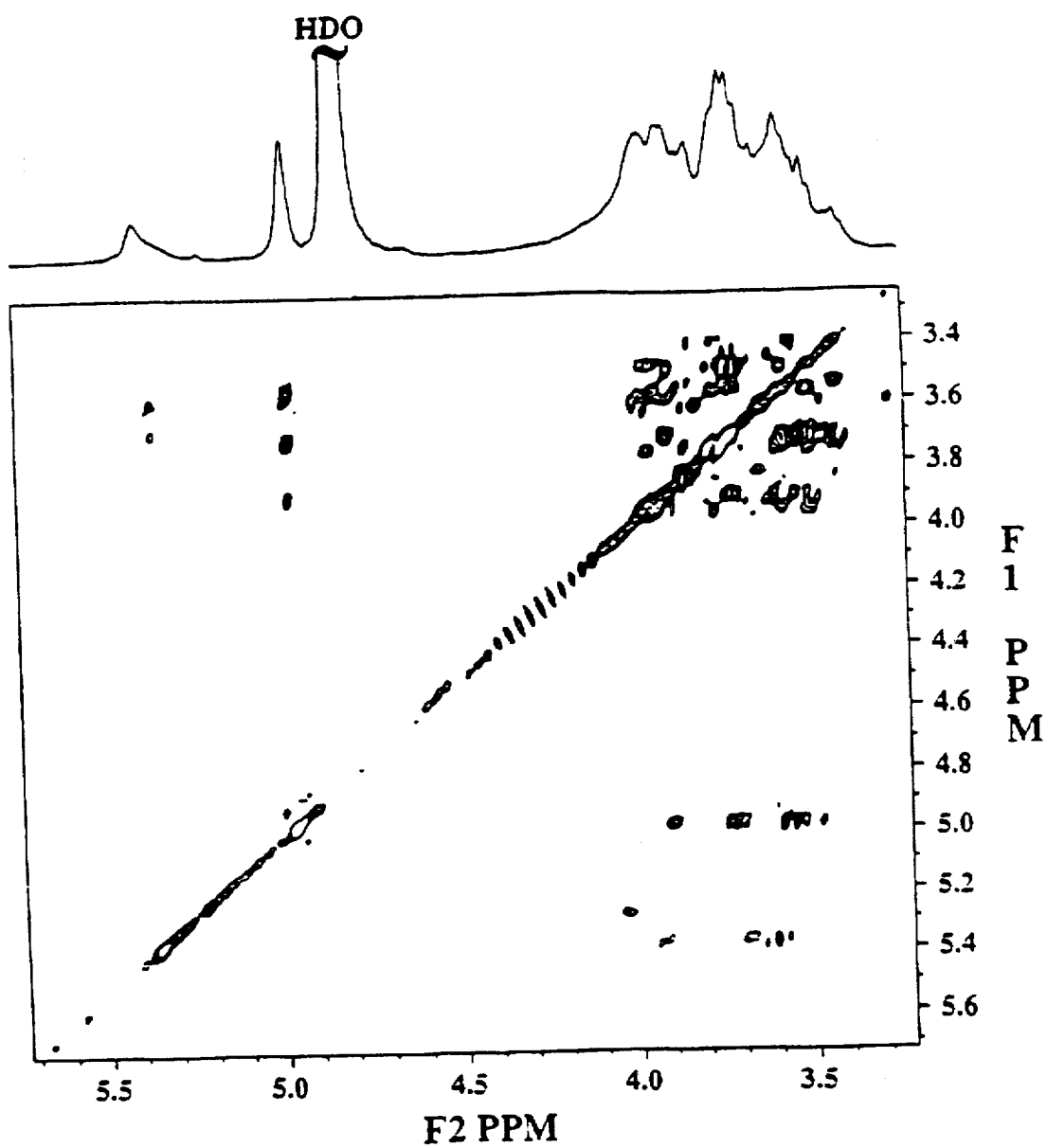
FIG. 9. The Homonuclear Hartmann-Hahn Spectrum of PS1A1.
Figure 11:
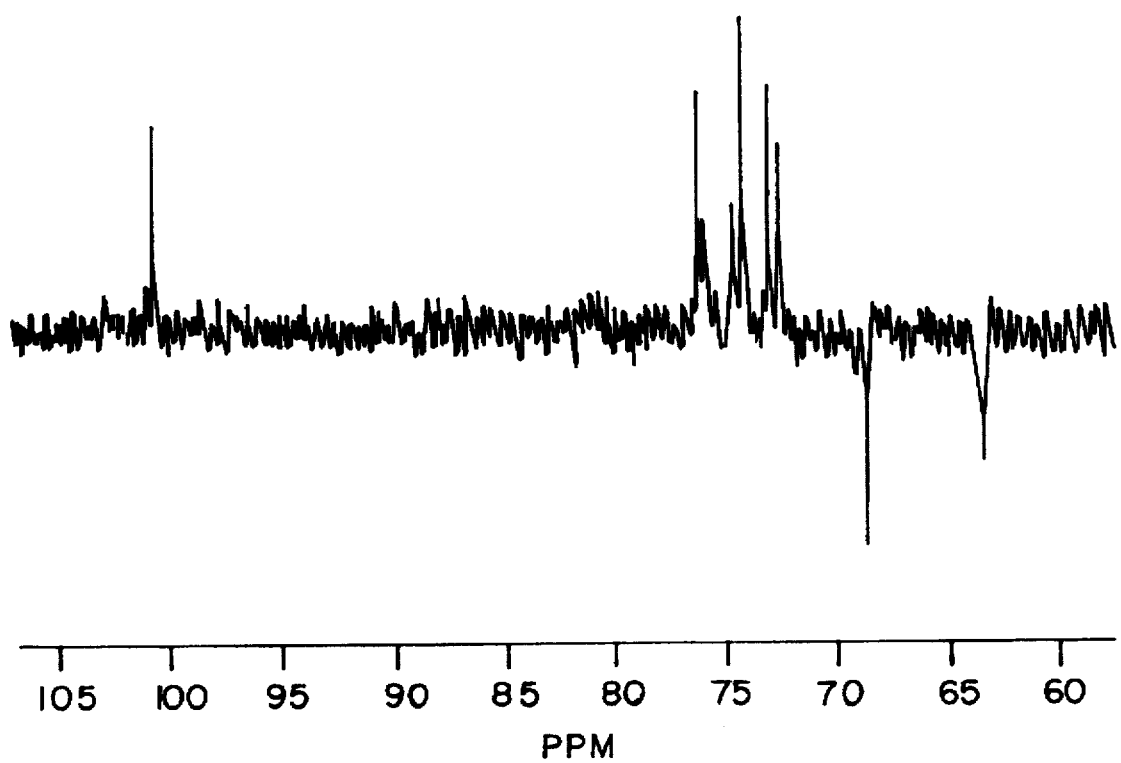
FIG. 11. The DEPT (135°) spectrum of PS1A1.

We claim:

1. A polymer extract having antitumor activity obtained from *Mycobacterium bovis* BCG (TICE substrain) comprising a plurality of α-D-glucopyranosyl-(1–6)-α-D-glucopyranose units and at least one α-D-glucopyranosyl-(1–4)-α-D-glucopyranose unit wherein the polymer has a molecular weight of from between 65 and 87 kDa.

2. The polymer extract of claim 1 having a molecular weight of between 64.5 and 67 kDa.

3. The polymer extract of claim 1 wherein said polymer extract possesses a molecular weight of approximately 67 kDa.

4. The polymer of claim 1 having the structure:

(→6)-α-D-Glcp(1→6)-α-D-Glcp(1→4)-α-D-Glcp(1→6)-α-D-Glcp(1→6)-α-D-Glcp(1→)$_n$
<pre>
                                                    6
                                                    ↑
                                                    1
                                                 -α-D-Glcp
</pre>

5. The polymer extract of claim 1 wherein the extract is an aqueous extract.

6. A pharmaceutical substance possessing antitumor activity comprising the polymer extract of claim 1 and a pharmaceutically acceptable carrier.

* * * * *